(12) United States Patent
Falk et al.

(10) Patent No.: US 10,124,148 B2
(45) Date of Patent: Nov. 13, 2018

(54) GUIDE EXTENSION CATHETER WITH TRACKABLE TIP AND RELATED METHODS OF USE

(71) Applicant: BOSTON SCIENTIFIC SCIMED, INC., Maple Grove, MN (US)

(72) Inventors: Wayne Falk, Minneapolis, MN (US); Joel M. Wasdyke, Eden Prairie, MN (US); Huisun Wang, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 368 days.

(21) Appl. No.: 13/946,830

(22) Filed: Jul. 19, 2013

(65) Prior Publication Data

US 2014/0025004 A1   Jan. 23, 2014

Related U.S. Application Data

(60) Provisional application No. 61/673,687, filed on Jul. 19, 2012.

(51) Int. Cl.
| | | |
|---|---|---|
| *A61M 25/01* | (2006.01) | |
| *A61M 25/10* | (2013.01) | |
| *A61M 25/04* | (2006.01) | |
| *A61M 25/00* | (2006.01) | |

(52) U.S. Cl.
CPC .... *A61M 25/0105* (2013.01); *A61M 25/0068* (2013.01); *A61M 25/0069* (2013.01); *A61M 25/0108* (2013.01); *A61M 25/04* (2013.01); *A61M 25/10* (2013.01); *A61M 25/005* (2013.01); *A61M 2025/0175* (2013.01)

(58) Field of Classification Search
CPC .......... A61M 25/0012; A61M 25/0108; A61M 2025/09166
USPC ....................................... 604/103.1
See application file for complete search history.

(56) References Cited

U.S. PATENT DOCUMENTS

| | | | |
|---|---|---|---|
| 4,564,014 | A | 1/1986 | Fogarty et al. |
| 4,616,652 | A | 10/1986 | Simpson |
| 4,762,129 | A | 8/1988 | Bonzel |
| 5,120,323 | A | 6/1992 | Shockey et al. |
| 5,232,445 | A | 8/1993 | Bonzel |
| 5,238,004 | A | 8/1993 | Sahatjian et al. |
| 5,267,982 | A | 12/1993 | Sylvanowicz |

(Continued)

FOREIGN PATENT DOCUMENTS

| | | |
|---|---|---|
| DE | 3819372 C1 | 1/1990 |
| EP | 0277366 A1 | 8/1988 |

(Continued)

*Primary Examiner* — Bhisma Mehta
*Assistant Examiner* — William Frehe
(74) *Attorney, Agent, or Firm* — Seager, Tufte & Wickhem LLP (57) ABSTRACT

Medical devices and methods for making and using medical devices are disclosed. An example medical device may include a guide extension catheter. The guide extension catheter may include a proximal shaft having a first outer diameter. A distal sheath may be attached to the proximal shaft and may have a second outer diameter greater than the first outer diameter. A trackable tip member may be attached to the distal sheath and extending distally therefrom. The trackable tip member may define a guidewire lumen therein.

14 Claims, 5 Drawing Sheets

(56) References Cited

U.S. PATENT DOCUMENTS

| | | | |
|---|---|---|---|
| 5,374,286 A * | 12/1994 | Morris | A61N 1/056 600/375 |
| 5,385,562 A | 1/1995 | Adams et al. | |
| 5,441,489 A | 8/1995 | Utsumi et al. | |
| 5,527,292 A | 6/1996 | Adams et al. | |
| 5,772,609 A | 6/1998 | Nguyen et al. | |
| 6,066,126 A | 5/2000 | Li et al. | |
| 6,139,510 A | 10/2000 | Palermo | |
| 6,508,803 B1 | 1/2003 | Horikawa et al. | |
| 6,575,958 B1 | 6/2003 | Happ et al. | |
| 6,638,268 B2 | 10/2003 | Niazi | |
| 6,695,793 B2 | 2/2004 | Brennan et al. | |
| 6,953,454 B2 | 10/2005 | Peterson et al. | |
| 7,294,124 B2 | 11/2007 | Eidenschink | |
| 7,316,678 B2 | 1/2008 | Nash et al. | |
| 7,717,899 B2 | 5/2010 | Bowe et al. | |
| 7,736,355 B2 | 6/2010 | Itou et al. | |
| 7,762,984 B2 | 7/2010 | Kumoyama et al. | |
| 7,892,215 B2 * | 2/2011 | Melsheimer | A61F 2/95 604/103.04 |
| 8,048,032 B2 | 11/2011 | Root et al. | |
| 8,142,413 B2 | 3/2012 | Root et al. | |
| 8,292,850 B2 | 10/2012 | Root et al. | |
| 9,017,309 B2 | 4/2015 | Tanikawa et al. | |
| 2004/0116832 A1 | 6/2004 | Friedrich et al. | |
| 2006/0282041 A1 | 12/2006 | Melsheimer et al. | |
| 2009/0177120 A1 | 7/2009 | Tockman et al. | |
| 2009/0264865 A1 | 10/2009 | Kawai | |
| 2010/0030186 A1 | 2/2010 | Stivland | |
| 2010/0036312 A1 | 2/2010 | Krolik et al. | |
| 2010/0217237 A1 * | 8/2010 | Itou | A61B 17/22 604/540 |
| 2010/0234876 A1 * | 9/2010 | Watson | 606/194 |

FOREIGN PATENT DOCUMENTS

| | | |
|---|---|---|
| EP | 1639951 A1 | 3/2006 |
| EP | 1656963 A1 | 5/2006 |
| EP | 2138200 A1 | 12/2009 |
| JP | 2006087643 A | 4/2006 |
| JP | 2007236632 A | 9/2007 |
| JP | 2009504343 A | 2/2009 |
| JP | 2009072294 A | 4/2009 |
| JP | 2010017211 A | 1/2010 |
| WO | 03049798 A2 | 6/2003 |
| WO | 2008123521 A1 | 10/2008 |

* cited by examiner

GUIDE EXTENSION CATHETER WITH TRACKABLE TIP AND RELATED METHODS OF USE

CROSS-REFERENCE TO RELATED APPLICATIONS

This application claims priority under 35 U.S.C. § 119 to U.S. Provisional Application Ser. No. 61/673,687, filed Jul. 19, 2012, the entirety of which is incorporated herein by reference.

TECHNICAL FIELD

The present disclosure pertains to medical devices and methods for manufacturing medical devices. More particularly, the present disclosure pertains to elongated intracorporeal medical devices including a guide extension catheter having a trackable tip.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device may include a guide extension catheter. The guide extension catheter may include a proximal shaft having a first outer diameter. A distal sheath may be attached to the proximal shaft and may have a second outer diameter greater than the first outer diameter. A trackable tip member may be attached to the distal sheath and extending distally therefrom. The trackable tip member may define a guidewire lumen therein.

An example guide extension catheter system is also disclosed. The guide extension catheter system may include a guide catheter having a lumen formed therein. A guide extension catheter may extend through the lumen. The guide extension catheter may include a proximal shaft having a first outer diameter. A distal sheath may be attached to the proximal shaft. The distal sheath may have a proximal opening, a distal opening, and a central lumen defined therebetween. The distal sheath may have a second outer diameter greater than the first outer diameter. A trackable tip member may be attached to the distal sheath and may extend distally therefrom. The trackable tip member define a guidewire lumen. A guidewire may extend through the central lumen of the distal sheath and through the guidewire lumen of the trackable tip member.

A method for crossing a constricted portion of a coronary artery is also disclosed. The method may include providing a guide catheter and advancing the guide catheter through a blood vessel to a position adjacent to an ostium of a coronary artery, and providing a guide extension catheter. The guide extension catheter may include a proximal shaft having a first outer diameter. A distal sheath may be attached to the proximal shaft. The distal sheath having a proximal opening, a distal opening, and a central lumen defined therebetween. The distal sheath may have a second outer diameter greater than the first outer diameter. A trackable tip member may be attached to the distal sheath and may extend distally therefrom. The trackable tip member may define a guidewire lumen therein. The method may also include advancing a guidewire through the guide catheter and advancing the guide extension catheter over a guidewire. Advancing the guide extension catheter over a guidewire may include disposing the guidewire within the guidewire lumen of the trackable tip member.

A method for accessing a coronary artery is also disclosed. The method may include providing a guide catheter, advancing the guide catheter through a blood vessel to a position adjacent to an ostium of a coronary artery, and providing a guide extension catheter. The guide extension catheter may include a proximal shaft having a first outer diameter. A distal sheath may be attached to the proximal shaft. The distal sheath having a proximal opening, a distal opening, and a central lumen defined therebetween. The distal sheath may have a second outer diameter greater than the first outer diameter. A trackable tip member may be attached to the distal sheath and may extend distally therefrom. The trackable tip member may define a guidewire lumen therein. The method may also include advancing the guide extension catheter through the guide catheter to a position where at least a portion of the trackable tip member extends distally beyond a distal end of the guide catheter and into the coronary artery, and advancing a treatment catheter through the guide catheter.

The above summary of some embodiments is not intended to describe each disclosed embodiment or every implementation of the present disclosure. The Figures, and Detailed Description, which follow, more particularly exemplify the embodiments of the present disclosure.

BRIEF DESCRIPTION OF THE DRAWINGS

The disclosure may be more completely understood in consideration of the following detailed description of various embodiments of the disclosure in connection with the accompanying drawings, in which.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with one embodiment, it should be understood that such feature, structure, or characteristic may also be used connection with other embodiments whether or not explicitly described unless cleared stated to the contrary.

Embodiments of the disclosure may include a guide extension catheter having a proximal shaft, distal sheath and a trackable tip member. The proximal shaft may attach to the distal sheath distally. At the distal end of the sheath, the trackable tip member may be disposed. The trackable tip member may have a diameter that is smaller than the diameter of the distal sheath. Additionally, the trackable tip member may have a guidewire lumen, the guidewire lumen of the trackable tip member is sized to closely track over a guidewire.

Many of the following examples illustrate implementations in which the guide extension catheter may be employed to cross a constricted portion of a coronary artery. It will be understood that this choice is merely exemplary and the guide extension catheter may be used in any desired body location requiring diagnostic or therapeutic modalities without departing from the scope of the present disclosure.

For purposes of this disclosure, "proximal" refers to the end closer to the device operator during use, and "distal" refers to the end further from the device operator during use.

Figure 1A:
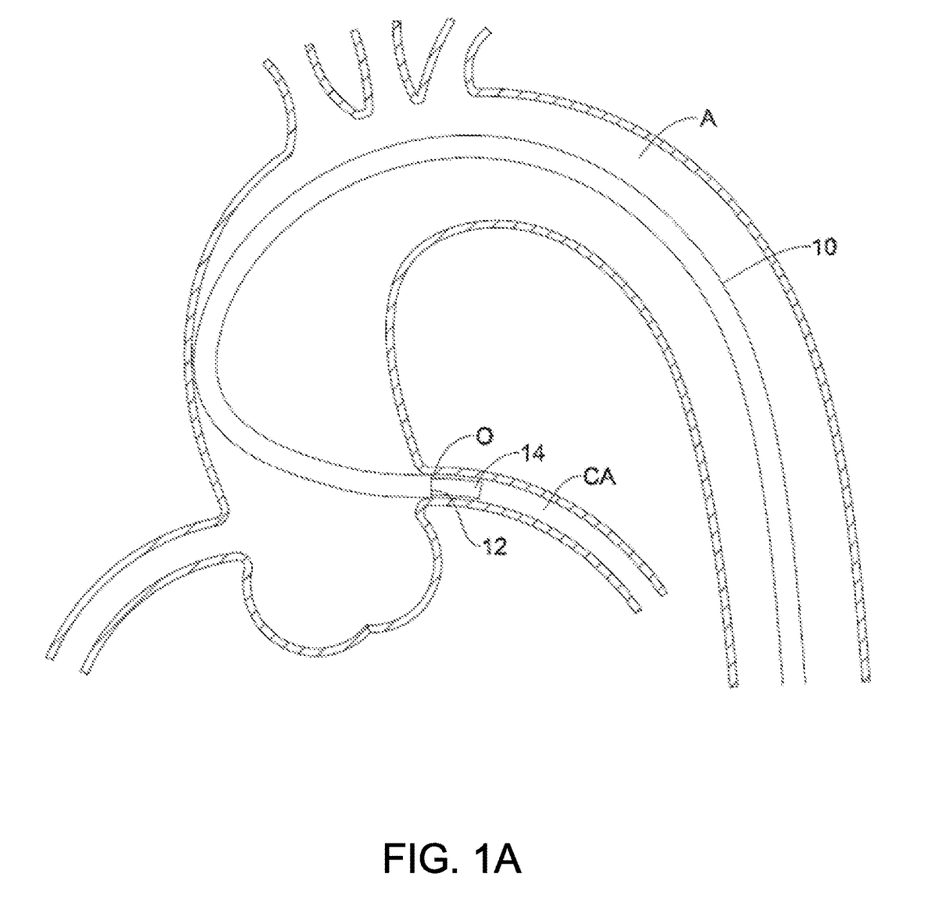
FIG. 1A is a plan view illustrating an example guide catheter with a guide extension catheter, advanced through the aorta to the ostium of a coronary artery.

Minimally-invasive cardiac interventions such as percutaneous transluminal coronary angioplasty are widely utilized throughout the world. These procedures may include the use of a guide catheter. For example, a guide catheter 10 may be advanced through a blood vessel such as the aorta A to a position adjacent to the ostium O of a (e.g., left and/or right) coronary artery CA as illustrated in FIG. 1A. When so positioned, a treatment catheter (e.g., balloon catheter, stent delivery system, etc.) may be advanced through guide catheter 10 and into the coronary artery CA to a target location where the treatment catheter may be used to perform the appropriate cardiac intervention.

In order for the treatment catheter to efficiently reach the intended target location, maintaining the position of guide catheter 10 at the ostium O of the coronary artery CA may be desirable. For example, given that the heart may be beating during the intervention (and/or other factors), the guide catheter 10 may lose its positioning or otherwise be shifted so that it no longer is positioned to efficiently guide the treatment catheter to the coronary arteries. This may include a distal end 12 of guide catheter 10 being shifted away from the ostium O of the coronary artery CA. Because of the shift away from the ostium O, access to the coronary arteries CA may require repositioning of guide catheter 10 in order to bring the distal end 12 back into engagement with the ostium O of the coronary artery CA.

Disclosed herein are medical devices and methods for making and using medical devices that may improve access to the coronary arteries CA. Here, a guide extension catheter 14 extends through guide catheter 10 and beyond distal end 12 of guide catheter 10 into the coronary artery CA. Because, for example, guide extension catheter 14 may extend beyond distal end 12 of guide catheter 10, guide extension catheter 14 may extend beyond the ostium O of the coronary artery CA and into a portion of the coronary artery CA. By extending beyond the ostium O, the extension catheter 14 may stabilize the positioning of guide catheter 10 and allow for improved access to the coronary artery CA for a number of cardiac interventions.

Figure 1B:
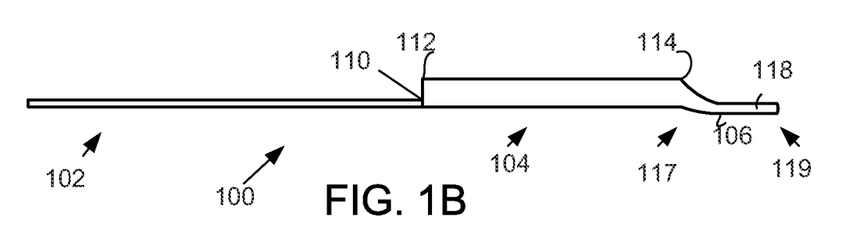
FIG. 1B is a plan view of a guide extension catheter according to the present disclosure.
Figure 1C:
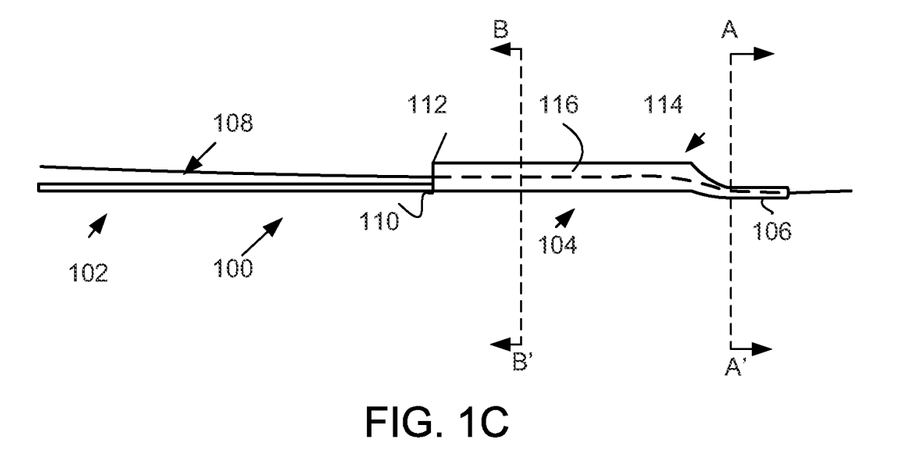
FIG. 1C is a plan view of a guide extension catheter according to the present disclosure, mounted on a guide wire.

FIGS. 1B-1C are plan views of a guide extension catheter 100 having a trackable tip, with the guide extension catheter 100 tracking on a guidewire 108, respectively. It has been observed that conventional guide extension catheters are often not able to cross through tortuous, stenosed, or calcified coronary vessels, owing to their large crossing profile. Also, the extensions generally available to the art often do not track tightly over the guidewire. If the guide extension catheter does not reach the desired location, the anchor balloon technique may be employed, but this technique may require a relatively large amount of force by an operator, and thus it may not be desirable.

FIG. 1B is a plan view of a guide extension catheter 100 having a trackable tip member 106. As noted above, guide extension catheter 100 may extend through a guide catheter 10 and into the coronary artery CA (FIG. 1A). For example, the guide extension catheter 100 may extend beyond the distal end of guide catheter 10 and may further extend beyond the ostium O of the coronary artery CA and into a portion of the coronary artery CA. As depicted in FIG. 1B, the guide extension catheter 100 may have a proximal shaft 102, a distal sheath 104 and the trackable tip member 106.

The proximal shaft 102 may be an elongate member coupled distally to the distal sheath 104 via appropriate coupling mechanism. Alternatively, the proximal shaft 102 may be a hypotube-like structure having a proximal end, a distal end 110, and a lumen defined therein. The lumen may extend along the entire length of the proximal shaft 102. In other embodiments, the lumen may extend along only a portion of the length of the proximal shaft 102. Further, the proximal shaft 102 may have a first outer diameter. Moreover, the shaft 102 may have any cross-sectional shape, such as cylindrical, circular, rhombic, rectangular, oval, semicircular, or the like, suitable for insertion into a guide catheter 10, as discussed above.

Distal sheath 104 may have a proximal end 112 and a distal end 114, with a central lumen 116 defined between those ends. The distal end 110 of proximal shaft 102 may attach to the proximal end 112. The proximal and distal ends 112, 114, may have a proximal opening and distal openings, respectively and these opening may define the central lumen 116 (See FIG. 1C). The central lumen 116 of the distal sheath 104 may be larger than the lumen of the proximal shaft 102. In particular, the central lumen 116 may be sufficiently large to allow a therapeutic device, such as a balloon catheter or stent delivery system, for example, to be carried through the central lumen 116. In other words, the central lumen 116 may be sized to accommodate any therapeutic device that is larger than the guidewire 108. Thus, when the guide extension catheter 100 is positioned within guide catheter 10, the therapeutic device may be disposed within central lumen 116. The distal sheath 104 may have a second outer diameter, size to be greater than the first outer diameter. The distal sheath 104 may have an outer diameter that approximates the inner diameter of a guide catheter 10 so that the guide extension catheter 100 may extend through the guide catheter 10 appropriately. The inner diameter of the distal sheath 104 may be sized to allow a guidewire to pass through. In some embodiments, the inner diameter of sheath 104 may be such that the therapeutic device can easily pass through. The distal sheath 104 may have a uniform cross-section or diameter from its proximal end 112 to the distal end 114, or that cross-section and diameter may vary through its length.

The precise form of the distal sheath 104 may vary. For example, in one embodiment, the distal sheath 104 may include a supporting member in the form of braid, rod, coil, mesh or similar structure. The distal sheath 104 may also include radiopaque material, either as a radiopaque marker band, as a polymeric material doped with radiopaque material, or the like. As discussed above, the distal sheath 104 may attach mechanically to the proximal shaft 102. In other embodiments, bonding mechanism including adhesive bonding, thermal bonding, welding, brazing, for example may be used. Also, a collar disposed at the distal end 110 of the proximal shaft 102 may be used to attach the distal sheath 104 to the proximal shaft 102. Other attachment mechanisms are contemplated.

Trackable tip member 106 lies at the distal end of guide extension catheter 100, in the form of a tubular snout or projection extending distally from the guide extension catheter 100. The trackable tip member 106 may be formed integrally with or may attach to the distal sheath 104. The trackable tip member 106 may have a proximal opening 117, a distal opening 119, and a guidewire lumen 118 extending between the proximal opening 117 and the distal opening 119. The proximal opening 117 may be disposed at or adjacent to the distal end 114 of the distal sheath 104. In some embodiments, the proximal opening 117 may be positioned within the central lumen 116 of the distal sheath 104.

The guidewire lumen 118 may open into the central lumen 116 of the distal sheath 104 and may extend distally to the end of trackable tip member 106. Here, the guidewire lumen 118 of the trackable tip member 106 may have a central axis that is parallel to and radially offset from a central axis of the central lumen 116 of the distal sheath 104 The trackable tip member 106 may have a smaller outer diameter than the distal sheath 104. Particularly, the trackable tip member 106 may have a third outer diameter that is smaller than the second outer diameter of the distal sheath 104. In addition, the trackable tip member may have a smaller inner diameter than the distal sheath 104 so that, for example, the diameter of the central lumen 116 approximates the outer diameter of the guidewire 108.

FIG. 1C is a plan view of the guide extension catheter 100, mounted on the guidewire 108. Here, the guidewire lumen 118 (FIG. 1B) may be smaller—such that it approximates the size of the guidewire 108. This design may allow the guide extension catheter 100 to track more easily over the guidewire 108. The guidewire 108 may first pass through the central lumen 116 of the distal sheath 104 and then through the guidewire lumen 118 of the trackable tip member 106. The guidewire lumen 118 may be configured with any shape suitable to accommodating the profile of the guidewire 108 in use for that application, such as circular, oval, polygonal, or irregular. The guidewire lumen 118 may have cross-sectional dimensions greater than the cross-sectional dimensions of the guidewire 108. Also, the cross-sectional dimensions of the guidewire lumen 118 may be less than the thickness of the blood vessel wall where the treatment catheter may be used. In one embodiment, the diameter of the guidewire lumen 118 may be about 0.01 to 0.04 inches (e.g., the guidewire lumen 118 may have a diameter that approximates the outer diameter of a standard guidewire such as a 0.014 or a 0.035 inch diameter guidewire) or may vary based on the configuration of the guide extension catheter 100.

Figure 1D:
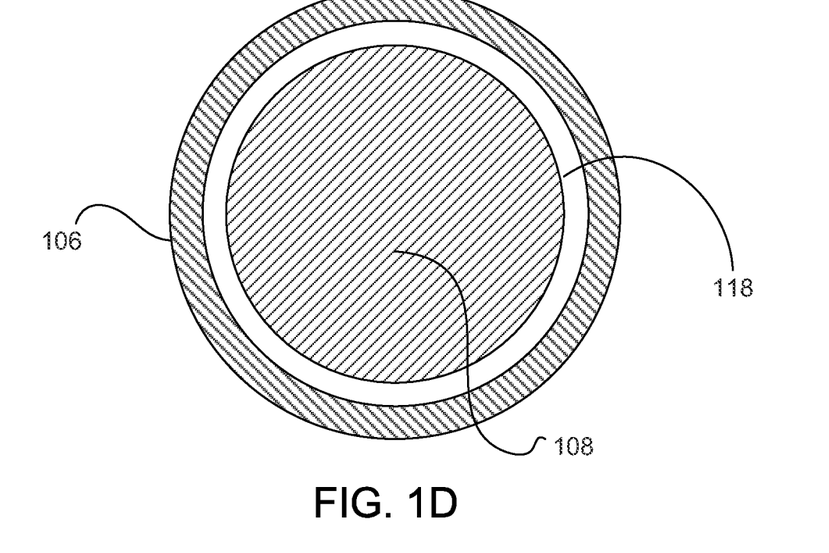
FIG. 1D is a cross-sectional view of trackable tip member of the guide extension catheter.

FIG. 1D shows a cross-sectional view of the trackable tip member 106, taken on plane A-A' of FIG. 1C with the guidewire 108 disposed in it. In particular, FIG. 1D shows a guidewire lumen 118 through which a guidewire 108 passes. The trackable tip member 106 is designed to track the guidewire 108 relatively tightly.

Figure 1E:
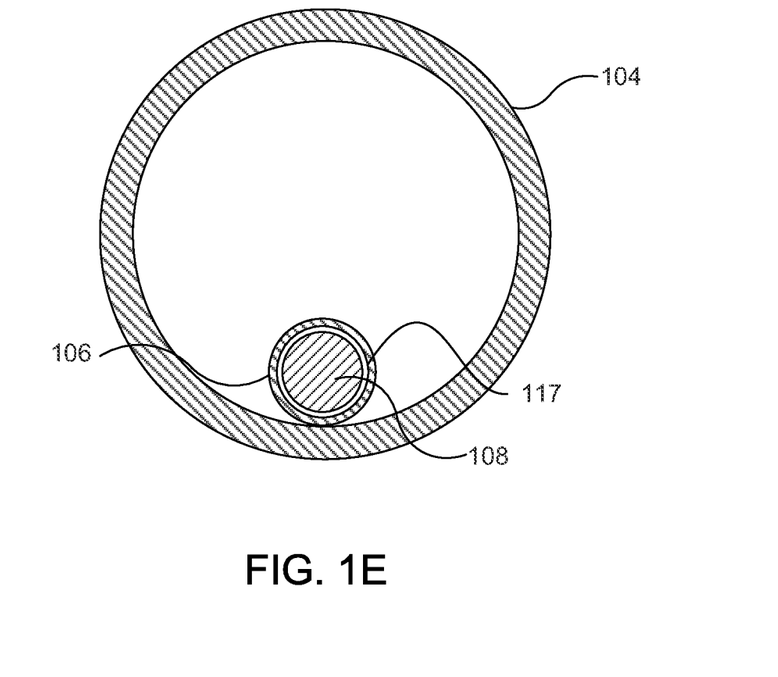
FIG. 1E is a cross-sectional view of guide extension catheter.

FIG. 1E is a cross-sectional-view of guide extension catheter 100 taken on plane B-B' of FIG. 1C. The tip member 106 may be visible when looking at the cross-section of the guide extension catheter 100 distally. This FIG. 1E shows the distal sheath 104 and the trackable tip member 106 and the guidewire 108 passing through the proximal opening 117 of the tip member 106. It can be appreciated that this drawing is schematic in nature as the guidewire 108 may also extend proximally within the distal sheath 104 (not shown) and proximally therefrom.

Additionally, guide extension catheter 100 (and/or portions thereof) may also include a number of coatings that may for example, reduce friction. For example, guide extension catheter 100 may have an inner and/or outer coating that includes a hydrophilic polymer that may reduce friction during tracking An example coating may include BAYER CL-100, BIOSLIDE, NG-HPC, SLIP COAT, MDX, or the like. These are just examples. Other materials are contemplated including those disclosed herein.

Figure 2A:
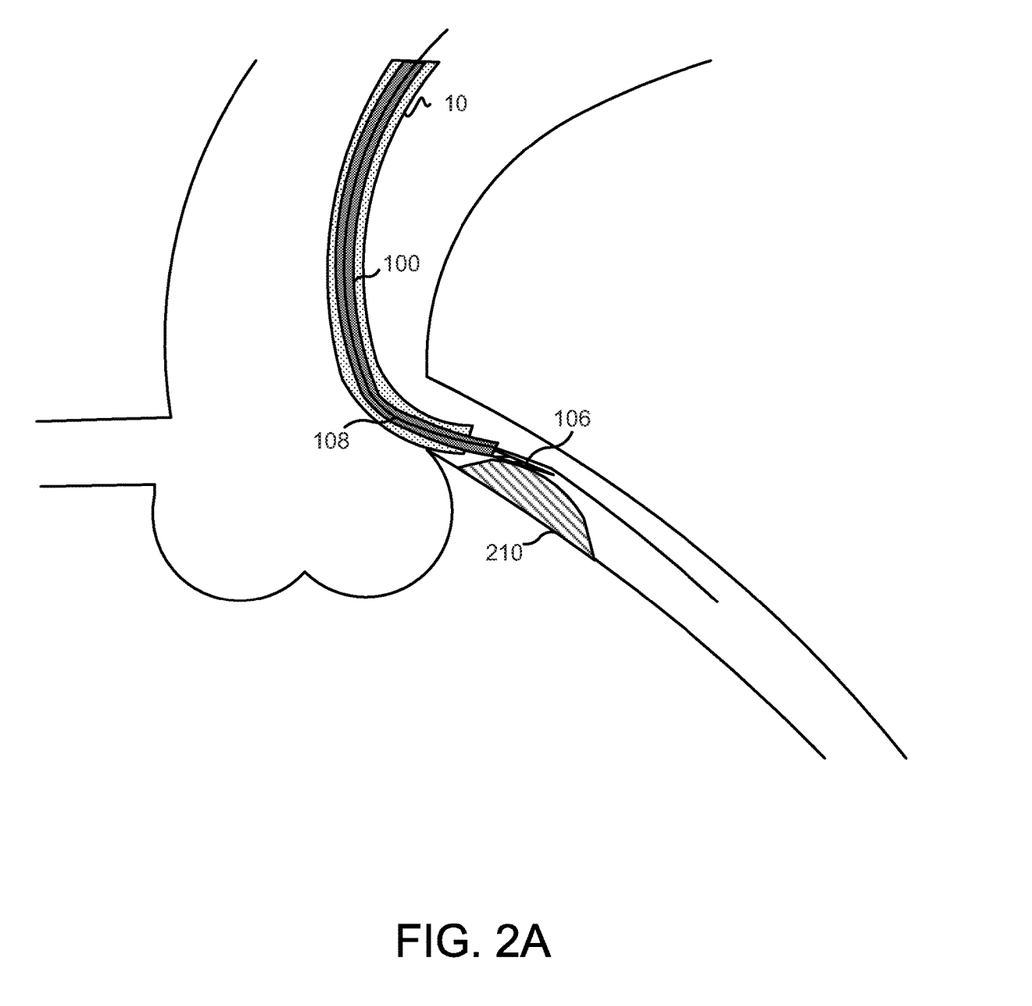
FIGS. 2A and 2B show exemplary medical device assemblies of the disclosure.
Figure 2B:
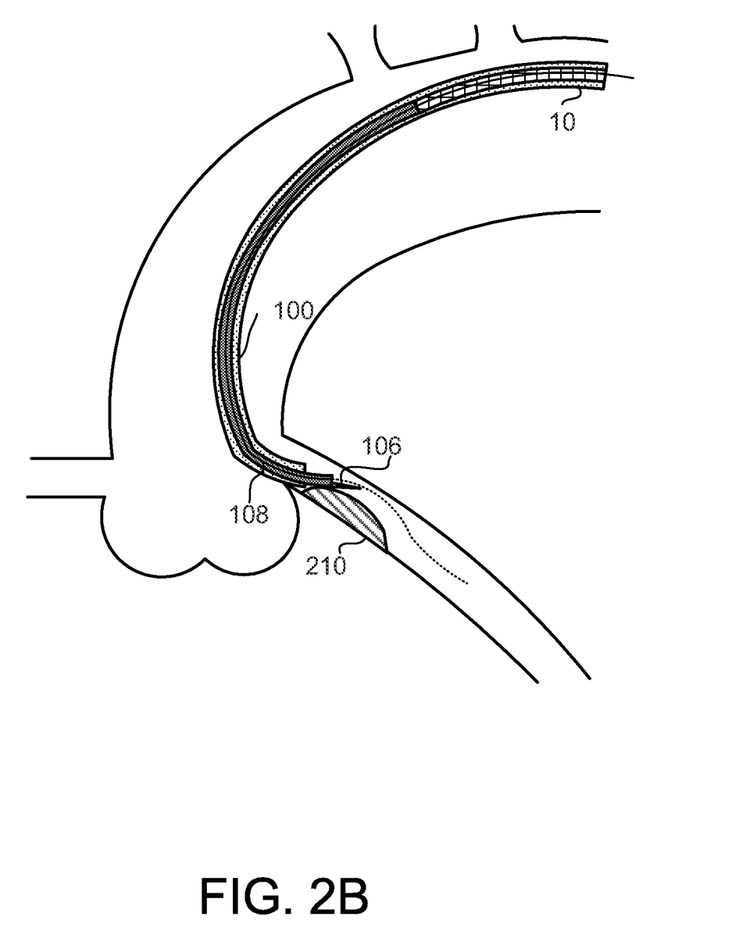

FIG. 2A shows a complete medical device assembly 200 having a guide catheter 10, guide extension catheter 100, and a guidewire 108. More specifically, FIG. 2A shows the use of medical device assembly 200 for crossing a constricted portion 210 of the coronary artery.

An exemplary method may include advancing the guide extension catheter 100 through a guide catheter 10 such that the guide extension catheter 100 extends beyond the distal end of the guide catheter 10 into the constricted portion 210 of the coronary artery. Further, the method may include advancing the guidewire 108 through the guide catheter 10. Then, the method may include advancing the guide extension catheter 100 over the guidewire 108 such that the trackable tip member 106 is advanced over the guidewire 108. The trackable tip member 106 may assist the guidewire 108 reaching the target coronary artery and/or aid in passing constricted portion 210. After positioning, the method may include proximally retracting guidewire 108 from the trackable tip member 106 (e.g., out from the proximal opening 117) and then distally out from distal sheath 104. Then, the therapeutic device, such as, balloon catheter, can be passed over the guidewire 108. In some of these and in alternative embodiments, a second guidewire may be passed through the distal sheath 104 and the therapeutic device may be passed over the second guidewire.

The medical device assembly including the guide extension catheter 100, guide catheter 10, and guidewire 108 or otherwise include metals, polymers, metal-polymer composites, and the like. Some examples of suitable metals and metal alloys include stainless steel, such as 304V, 304 L, and 316 LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenyleneterephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. These are just examples.

Although the embodiments described above use guide extension catheter, those of skill in the art will understand that the principles set out there can be applied to any device where it is deemed advantageous to track guide extension catheter easily over a guidewire. Conversely, constructional details, including manufacturing techniques and materials, are well within the understanding of those of skill in the art and have not been set out in any detail here. These and other modifications and variations may well within the scope of the present disclosure can be envisioned and implemented by those of skill in the art.

Other embodiments of the present disclosure will be apparent to those skilled in the art from consideration of the specification and practice of the embodiments disclosed herein. It is intended that the specification and examples be considered as exemplary only, and departure in form and detail may be made without departing from the scope and spirit of the present disclosure as described in the following claims.

What is claimed is:

1. A guide extension catheter, comprising:
   a proximal shaft having a first outer diameter;
   a distal sheath attached to and extending from a distal end of the proximal shaft, the distal sheath having a second outer diameter greater than the first outer diameter; and
   a trackable tip member attached to and axially fixed with respect to the distal sheath and extending distally therefrom, the trackable tip member defining a guidewire lumen therein; and
   wherein the distal sheath has a first central axis and the trackable tip member has a second central axis parallel to and radially offset from the first central axis.

2. The guide extension catheter of claim 1, wherein the trackable tip member includes a radiopaque material.

3. The guide extension catheter of claim 1, wherein the trackable tip member has a proximal opening and a distal opening, and wherein the proximal opening is positioned at a distal end of the distal sheath.

4. The guide extension catheter of claim 1, wherein the trackable tip member has a third outer diameter that is smaller than the second outer diameter.

5. The guide extension catheter of claim 1, wherein the guidewire lumen of the trackable tip member is sized so that the trackable tip member is configured to closely track over a guidewire.

6. The guide extension catheter of claim 1, wherein the guidewire lumen has a diameter of 0.01 to 0.04 inches.

7. The guide extension catheter of claim 1, wherein the distal sheath includes a support member.

8. The guide extension catheter of claim 1, wherein the distal sheath includes a radiopaque material.

9. A medical device assembly, comprising:
   a guide catheter having a lumen formed therein;
   a guide extension catheter extending through the lumen, the guide extension catheter including:
      a proximal shaft having a first outer diameter;
      a distal sheath attached to the proximal shaft, the distal sheath having a proximal opening, a distal opening, and a central lumen defined therebetween and having a first central axis;
      wherein the distal sheath has a second outer diameter greater than the first outer diameter; and
      a trackable tip member attached to and axially fixed with respect to the distal sheath and extending distally therefrom, the trackable tip member defining a guidewire lumen therein and having a second central axis parallel to and radially offset from the first central axis; and a guidewire extending through the central lumen of the distal sheath and through the guidewire lumen of the trackable tip member.

10. The assembly of claim 9, wherein the trackable tip member includes radiopaque material.

11. The assembly of claim 9, wherein the trackable tip member has a proximal opening and a distal opening, and wherein the proximal opening is positioned at a distal end of the distal sheath.

12. The assembly of claim 9, wherein the trackable tip member has a third outer diameter that is smaller than the second outer diameter.

13. The assembly of claim 9, wherein the guidewire lumen of the trackable tip member is sized so that the trackable tip member is configured to closely track over the guidewire.

14. The assembly of claim 9, wherein the guidewire lumen has a diameter of 0.01 to 0.04 inches.

\* \* \* \* \*